United States Patent
Gohno

(10) Patent No.: US 7,382,858 B2
(45) Date of Patent: Jun. 3, 2008

(54) RADIATION IMAGING APPARATUS

(75) Inventor: Makoto Gohno, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 10 days.

(21) Appl. No.: 11/284,174

(22) Filed: Nov. 21, 2005

(65) Prior Publication Data

US 2006/0109954 A1 May 25, 2006

(30) Foreign Application Priority Data

Nov. 25, 2004 (JP) ............................. 2004-339772

(51) Int. Cl.
*H05G 1/64* (2006.01)
(52) U.S. Cl. .................. 378/98.12; 378/42; 378/209
(58) Field of Classification Search ............ 378/42, 378/62, 98.8–98.12, 109, 110, 208, 209; 382/132, 274; 250/370.09
See application file for complete search history.

(56) References Cited

U.S. PATENT DOCUMENTS

| 3,980,288 | A |   | 9/1976 | Mitchell et al. |
|---|---|---|---|---|
| 4,197,465 | A |   | 4/1980 | Schneider |
| 4,484,343 | A |   | 11/1984 | Cesar |
| 4,503,844 | A |   | 3/1985 | Siczek |
| 4,550,421 | A |   | 10/1985 | Louiday |
| 5,347,570 | A | * | 9/1994 | Haaks .................. 378/98.12 |
| 5,475,885 | A |   | 12/1995 | Ishikawa |
| 5,631,942 | A | * | 5/1997 | Shinoda .................. 378/98.12 |
| 5,825,843 | A |   | 10/1998 | Kobayashi |
| RE36,415 | E |   | 11/1999 | McKenna |
| 6,457,858 | B1 | * | 10/2002 | Nakamura et al. .......... 378/196 |
| 6,577,889 | B2 | * | 6/2003 | Ichihashi .................. 600/425 |
| 6,816,567 | B2 | * | 11/2004 | Drummond et al. .......... 378/16 |
| 6,912,415 | B2 | * | 6/2005 | Kruger et al. .............. 600/410 |
| 6,977,984 | B2 | * | 12/2005 | Hsieh et al. .................. 378/4 |
| 2002/0104163 | A1 |   | 8/2002 | Rolf |
| 2004/0141591 | A1 |   | 7/2004 | Izuhara |
| 2004/0172145 | A1 |   | 9/2004 | Varadharajulu |
| 2004/0261176 | A1 |   | 12/2004 | Jurgen |
| 2005/0084074 | A1 |   | 4/2005 | Varadharajulu |
| 2006/0233296 | A1 | * | 10/2006 | Wakai et al. .................. 378/8 |

FOREIGN PATENT DOCUMENTS

| JP | 05004150 | 1/1993 |
|---|---|---|
| JP | 08-336526 | 12/1996 |
| JP | 2001-212128 | 8/2001 |
| JP | 2002-177263 | 6/2002 |
| JP | 2004-208953 | 7/2004 |

OTHER PUBLICATIONS

Shinichi Iiasuku et al.; Patent Application "Transportation Apparatus and Tomography System"; Filed Nov. 16, 2005; 29 pgs.

* cited by examiner

*Primary Examiner*—Jurie Yun
(74) *Attorney, Agent, or Firm*—Armstrong Teasdale LLP

(57) ABSTRACT

With the object of enhancing operability and executing imaging efficiently, a moving speed adjustment unit adjusts a speed at which a table section is moved within an imaging space of a scanning gantry, on the basis of a command from an operator when the scanning gantry scans a subject.

11 Claims, 7 Drawing Sheets

FIG. 6A  FIG. 6B  FIG. 6C
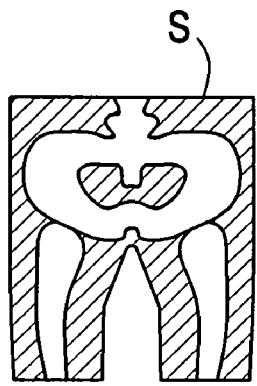
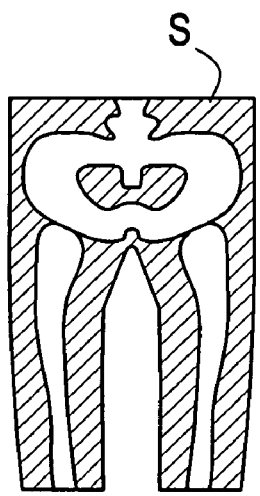
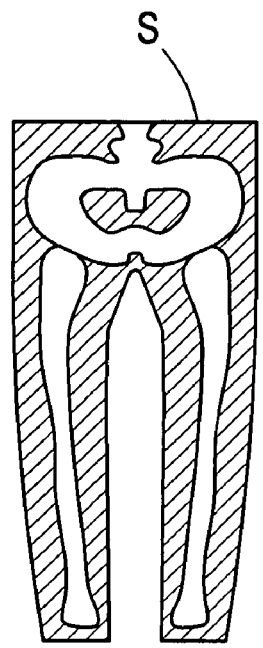
FIG. 7A  FIG. 7B
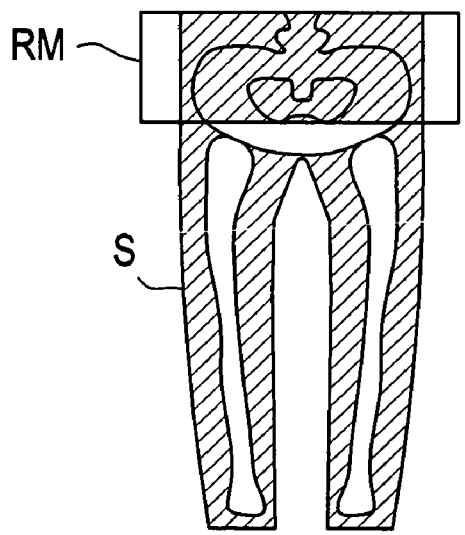
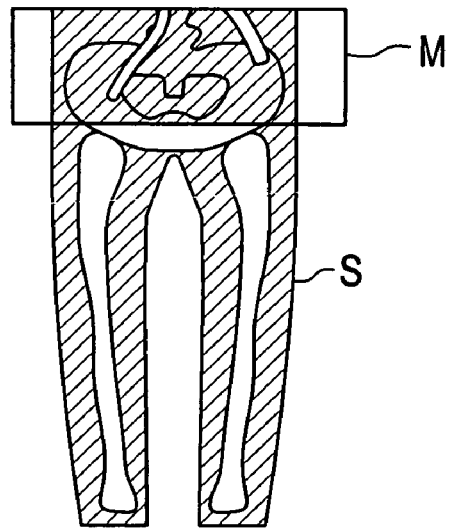

RADIATION IMAGING APPARATUS

CROSS REFERENCE TO RELATED APPLICATIONS

This application claims the benefit of Japanese Application No. 2004-339772 filed Nov. 25, 2004.

BACKGROUND OF THE INVENTION

The present invention relates to a radiation imaging apparatus, and particularly to a radiation imaging apparatus which scans a subject with radiation to acquire projection data and reconstructs the acquired projection data to generate an image of the subject.

A radiation imaging apparatus such as an X-ray CT (Computed Tomography) apparatus moves a subject to an imaging space and scans the subject moved into the imaging space with radiation to acquire projection data of the subject and generates an image about a tomographic plane of the subject on the basis of the acquired projection data. The X-ray CT apparatus has been utilized for a wide range of uses such as a medical use, an industrial use, etc.

In the X-ray CT apparatus, a table section supports the subject and a table moving section moves the table section to an imaging or photographing space. A scan section scans the subject moved to the imaging space by the table moving section and supported by the table section. In the X-ray CT apparatus, an X-ray tube and an X-ray detector are rotated with the direction of a body axis of the subject as the center. The X-ray tube applies X rays from the periphery of the subject along a plurality of view directions. The X-ray detector acquires projection data corresponding to the respective view directions as projection data. Further, the X-ray CT apparatus reconstructs and generates an image about a tomographic plane of the subject on the basis of the projection data from the respective view directions (refer to, for example, a patent document 1).

[Patent Document 1] Japanese Unexamined Patent Publication No. Hei 8(1996)-336526

There is a case in which upon imaging the subject using the X-ray CT apparatus, a contrast agent is administrated in the subject to execute its imaging.

When the contrast agent is administrated in the subject to carry out its imaging, the table moving section moves the table section so as to correspond to the state of progress or traveling of the contrast agent in the subject. In this case, the state of traveling of the contrast agent in the subject is estimated and the table section is moved such that its position is shifted at a constant speed. Therefore, there was a case in which each image of the subject based on the contrast agent could not imaged or photographed without coincidence thereof with the speed of the contrast agent that travels in the blood vessels of the subject.

When the contrast agent is administrated in the subject to carry out its imaging, images about an axial plane vertical to the body axial direction of the subject are displayed in real time in association with a plurality of slice positions. An operator is caused to recognize the state of progress of the contrast agent. Therefore, when the contrast agent travels in the direction along the body axial direction as in a foot part of the subject, it is difficult for the operator to recognize the state of progress of the contras agent. There is a case in which it is difficult to confirm whether imaging is done corresponding to the state of progress of the contrast agent.

Thus, the radiation imaging apparatus such as the X-ray CT apparatus does not have sufficient operability when the contrast agent is administrated in the subject to carry out its imaging, and encounters difficulties in carrying out the imaging efficiently.

The present invention relates to a radiation CT system such as an X-ray CT system, a data acquisition system, and a data acquisition method.

Radiation CT systems employing a multi-array detector that has a plurality of detector elements set in array in a direction of channels and in a direction of slices alike are known (refer to, for example, Patent Document 1). Output signals of the detector elements are amplified by amplifiers included in a data acquisition system (DAS). In general, the number of amplifiers is the same as the number of detector elements (the number of channels by the number of arrays juxtaposed in the direction of slices).

Patent Document 1 describes that four data acquisition systems (DASs) are used in combination with a multi-array detector having eight arrays of detector elements juxtaposed in the direction of slices, that the connections between the arrays of detector elements and the data acquisition systems are changed based on a slice thickness, and that one amplifier amplifies outputs of two arrays of detector elements. Herein, the connections are changed from ones to others prior to scanning, and two arrays of detector elements are treated as one array of detector elements. This is equivalent to a case where the same number of amplifiers as the number of detector elements is included.

[Patent Document 1] Japanese Unexamined Patent Publication No. 2001-212128

As for a multi-array detector, an increase in the number of arrays of detector elements juxtaposed in the direction of slices or realization of finer detector elements, that is, an increase in the number of detector elements is demanded from the viewpoint of a shorter scan time or improved image quality. On the other hand, amplifiers are included in a data acquisition system in association with all detector elements. The number of amplifiers increases along with an increase in the number of detector elements, whereby various drawbacks take place. For example, it is hard to preserve a space in which the amplifiers are disposed, a power consumption increases, an amount of dissipated heat increases, and a cost increases.

SUMMARY OF THE INVENTION

Thus, an object of the present invention is to provide a radiation imaging apparatus capable of enhancing operability and carrying out imaging efficiently.

In order to attain the above object, a radiation imaging apparatus of the present invention comprises a table unit which supports a subject to be examined, a table mover which moves the table unit in an imaging space, a scan section which scans the subject supported by the table unit in the imaging space with radiation to obtain projection data of the subject, an image generator which reconstructs the projection data obtained by the scan section to generate an image of the subject, and a displayer which displays the image of the subject generated by the image generator, wherein the scan section executes a first scan for applying the radiation to an imaging region for the subject to generate first projection data as the projection data and thereafter executes a second scan for applying the radiation to the imaging region for the subject with a contrast agent administrated therein to generate second projection data as the projection data, wherein the image generator reconstructs a first image about a section of the subject along the direction in which the table unit is moved, on the basis of the first projection data and thereafter reconstructs a second image about a section of the subject, corresponding to the first image on the basis of the second projection data in real time with respect to the execution of the second scan, and generates a third image on the basis of differential data based on substruction processing between the first image and the second image, and wherein the displayer displays the third image generated by the image generator in real time with respect to the execution of the second scan.

In order to attain the above object, a radiation imaging apparatus of the present invention comprises a table unit which supports a subject to be examined, a table mover which moves the table unit in an imaging space, a scan section which scans the subject supported by the table unit in the imaging space with radiation to obtain projection data of the subject, an image generator which reconstructs the projection data obtained by the scan section in real time to generate an image of the subject, and a displayer which displays the image of the subject generated by the image generator in real time, wherein the table mover has a speed adjustment unit which adjusts the moving speed of the table unit when the scan section scans the subject.

According to the present invention, a radiation imaging apparatus can be provided which is capable of enhancing operability and carrying out imaging efficiently.

Further objects and advantages of the present invention will be apparent from the following description of the preferred embodiments of the invention as illustrated in the accompanying drawings.

BRIEF DESCRIPTION OF THE DRAWINGS

FIG. 6A is a diagram showing an embodiment of a positioning image according to the present invention.

FIG. 6B is a diagram showing an embodiment of another positioning image generating by using the X-ray CT apparatus.

FIG. 6C is a diagram showing an embodiment of yet another positioning image generating by using the X-ray CT apparatus.

FIG. 7A is a diagram of an embodiment of a region of a subject subjected to a monitor scan.

FIG. 7B is a diagram illustrating an embodiment of a monitor image generated by executing the monitor scan.

DETAILED DESCRIPTION OF THE INVENTION

An embodiment according to the present invention will be explained.

Figure 1:
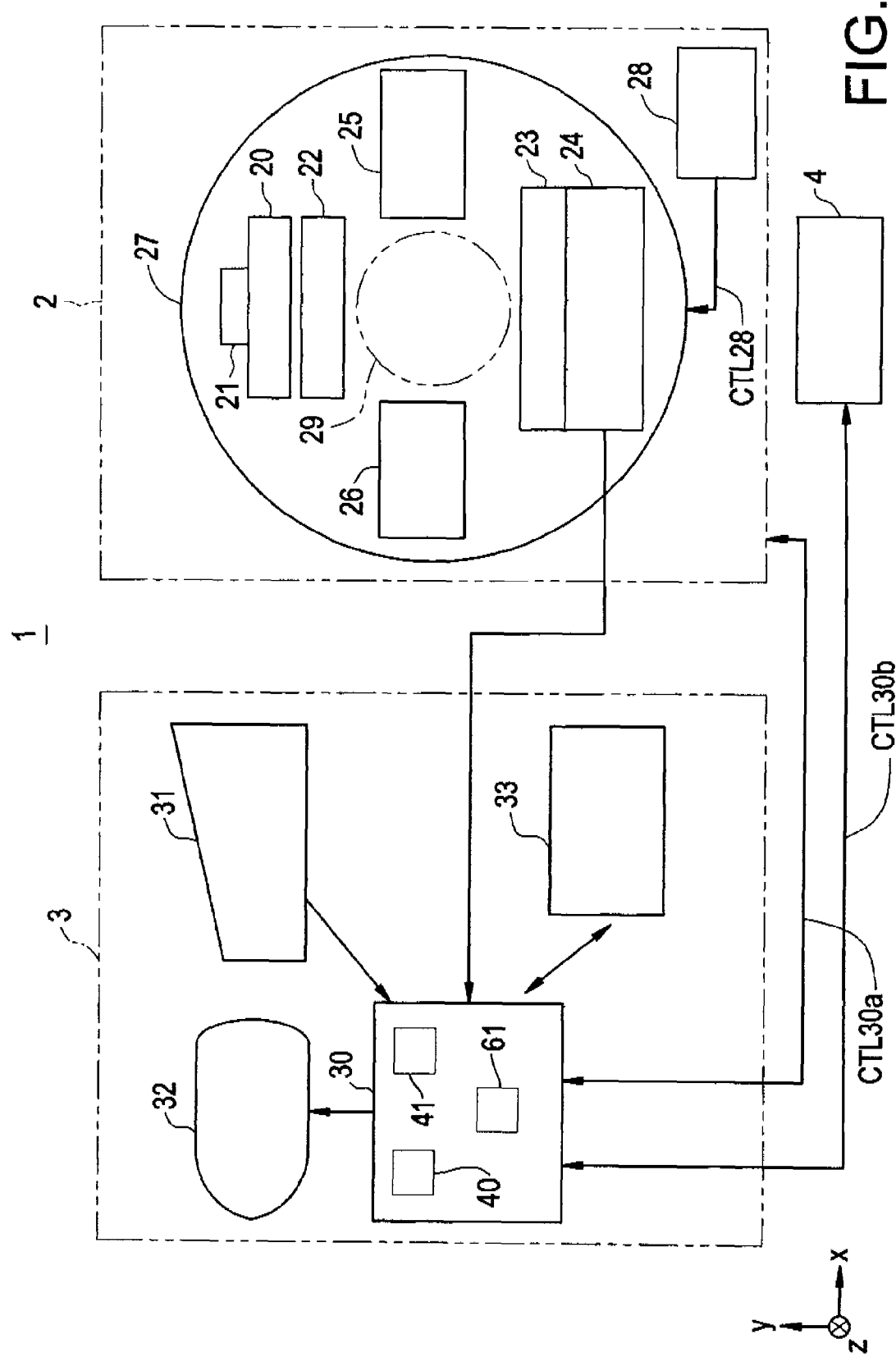
FIG. 1 is a block diagram showing an overall construction of an X-ray CT apparatus illustrative of an embodiment according to the present invention.
Figure 2:
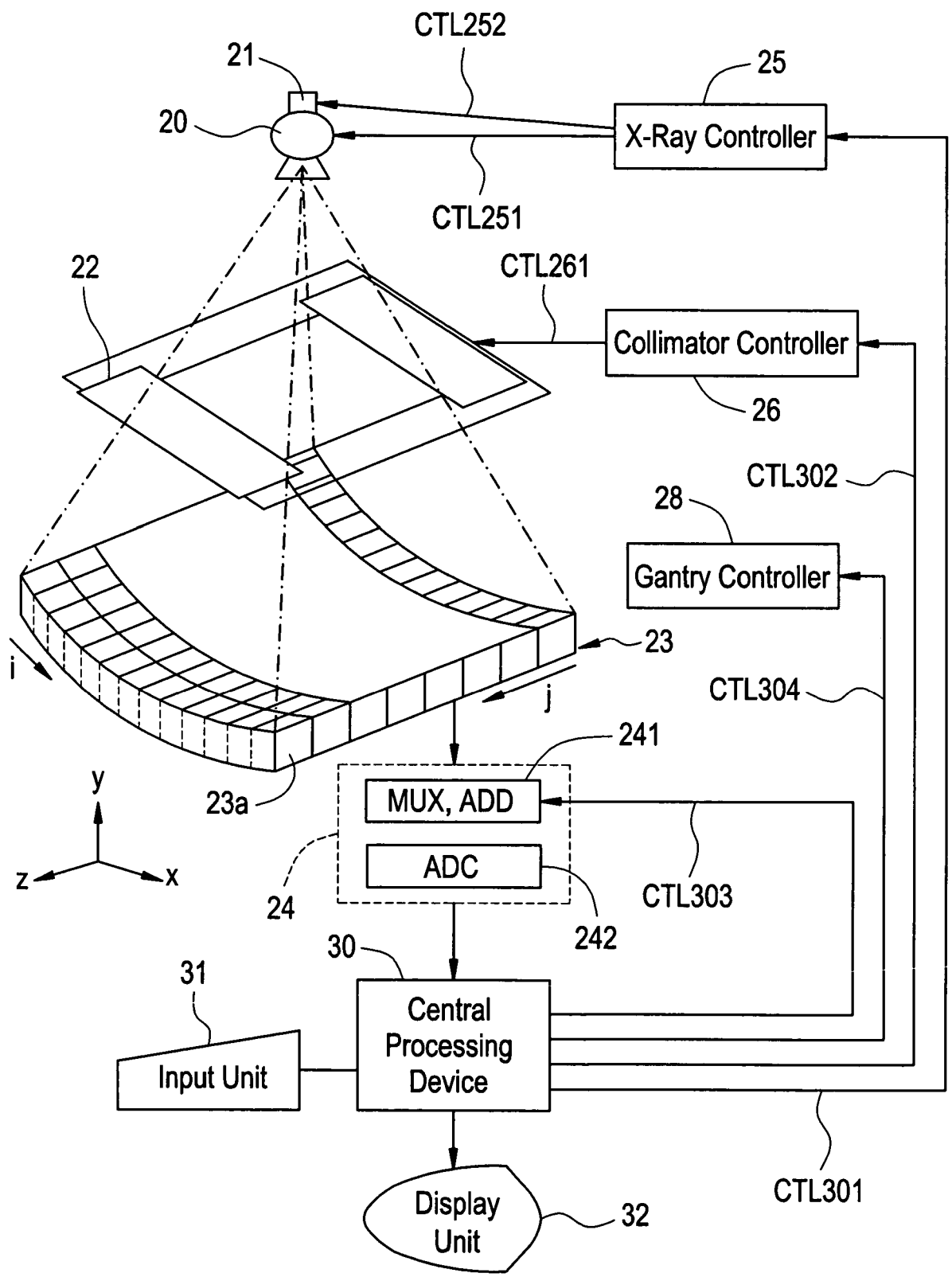
FIG. 2 is a configuration diagram illustrating an essential part of the X-ray CT apparatus illustrative of the embodiment according to the present invention.

FIG. 1 is a block diagram showing an overall construction of an X-ray CT apparatus 1 used as a radiation imaging apparatus illustrative of the embodiment according to the present invention, and FIG. 2 is a configuration diagram showing an essential part of the X-ray CT apparatus 1 of the present embodiment, respectively.

As shown in FIG. 1, the X-ray CT apparatus 1 includes a scanning gantry 2, an operation console 3 and a subject conveyer 4.

The scanning gantry 2 has an X-ray tube 20, an X-ray tube moving section 21, a collimator 22, an X-ray detector 23, a data acquisition section 24, an X-ray controller 25, a collimator controller 26, a rotational section 27 and a gantry controller 28. In the scanning gantry 2, a table moving section 102 of the subject conveyer 4 to be described later moves a table section 101 in an imaging space 29 and scans a subject supported by the table section 101 using X rays to obtain projection data of the subject as row data. For example, the scanning gantry 2 helically scans the subject in which a contrast agent is administrated.

In the present embodiment, the scanning gantry 2 first executes a positioning scan for applying X rays to an imaging region of the subject to generate first projection data as projection data. Thereafter, a contrast agent is administrated into the subject. Then, the scanning gantry 2 executes a main scan for applying X rays to the imaging region of the subject with the contrast agent administrated therein to generate second projection data as projection data. Here, the scanning gantry 2 performs the positioning scan and the main scan so as to helically scan the periphery of the subject along the direction in which the table section 101 is moved. That is, the scanning gantry 2 executes the positioning scan and the main scan according to a helical scan system.

Figure 3:
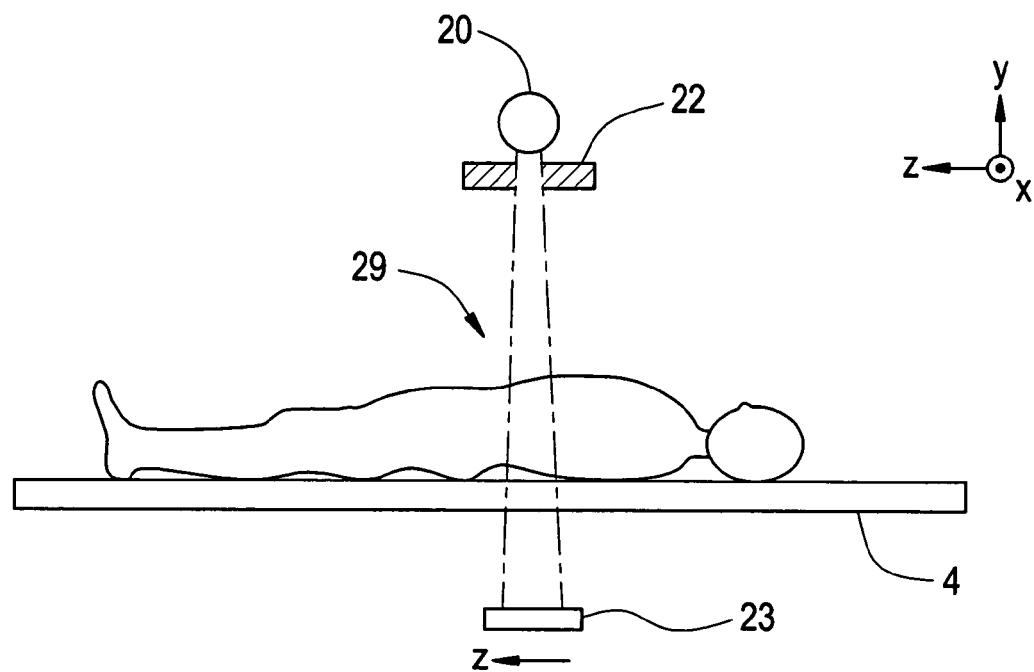
FIG. 3 is a diagram showing the relationship of a layout among an X-ray tube, a collimator and an X-ray detector in a scanning gantry of the X-ray CT apparatus illustrative of the embodiment according to the present invention.

FIG. 3 is a diagram showing the relationship of a layout among the X-ray tube 20, the collimator 22 and the X-ray detector 23 in the scanning gantry 2.

In the scanning gantry 2, as shown in FIG. 3, the X-ray tube 20 and the X-ray detector 23 are disposed so as to interpose the imaging space 29 in which the subject is carried, therebetween. The collimator 22 is disposed so as to form X rays from the X-ray tube 20.

The respective parts of the scanning gantry 2 will be explained.

The X-ray tube 20 is of, for example, a rotating anode type and applies X rays according to tube current values. As shown in FIG. 2, the X-ray tube 20 applies X rays of predetermined intensity to an imaging region of the subject via the collimator 22, based on a control signal CTL251 outputted from the X-ray controller 25. The X rays radiated from the X-ray tube 20 are shaped in the form of, for example, a cone by the collimator 22 and applied to the X-ray detector 23. Since the X-ray tube 20 applies the X rays to the subject from view directions as viewed in the periphery of the subject, the X-ray tube 20 rotates about the subject by the rotational section 27 with a body axial direction z of the subject as the axis. That is, the X-ray tube 20 turns around the subject about the axis along the direction in which the subject conveyer 4 moves the subject in the imaging space 29. In the present embodiment, the X-ray tube 20 applies the X rays on the basis of tube current values adjusted by a tube current adjustment part 40 in a central processing unit 30 of an operation console 3 to be described later according to the speed of the subject moved in a horizontal direction H by the subject conveyer 4.

As shown in FIG. 2, the X-ray tube moving section 21 moves the center of radiation of the X-ray tube 20 in the body axial direction z of the subject in the imaging space 29 of the scanning gantry 2 on the basis of a control signal CTL252 outputted from the X-ray controller 25.

As shown in FIG. 2, the collimator 22 is disposed between the X-ray tube 20 and the X-ray detector 23. The collimator 22 is constituted of plates respectively provided two by two in a channel direction i and a row direction j. The collimator 22 moves the two plates provided in the respective directions independently on the basis of a control signal CTL261 outputted from the collimator controller 26 and blocks or cuts off the X rays radiated from the X-ray tube 20 as viewed in the respective directions to shape the X rays in cone form, thereby adjusting the range of radiation of the X rays.

The X-ray detector 23 detects the X rays radiated from the X-ray tube 20 and transmitted through the subject and generates projection data of the subject. The X-ray detector 23 rotates about the subject together with the X-ray tube 20 by virtue of the rotational section 27. And the X-ray detector 23 detects the X rays radiated from the periphery of the subject and transmitted through the subject to generate projection data.

The X-ray detector 23 comprises a plurality of detecting elements 23a as shown in FIG. 2. In the X-ray detector 23, the detecting elements 23a are two-dimensionally laid out in array form in the channel direction i extending along the direction in which the X-ray tube 20 rotates around the subject by virtue of the rotational section 27 with the body axial direction z of the subject as the center and in the row direction j extending along the direction of a rotational axis used as a central axis when the X-ray tube 20 is rotated by the rotational section 27. The X-ray detector 23 has a cylindrical plane bent in a concave form, which is formed by the plurality of two-dimensionally arranged detecting elements 23.

The detecting elements 23a that constitute the X-ray detector 23 has, for example, scintillators (not shown) which transduce the detected X rays into light, and photo diodes (not shown) which convert the light transduced by the scintillators to electrical charges. The X-ray detector 23 is configured as a solid-state detector. Incidentally, each of the detecting elements 23a is not limited to above but may be, for example, a semiconductor detecting element using cadmium telluride (CdTe) or an ion chamber type detecting element 23a using a xenon (Xe) gas.

The data acquisition section 24 is provided to collect or acquire projection data from the X-ray detector 23. The data acquisition section 24 collects the projection data detected by the respective detecting elements 23a of the X-ray detector 23 and outputs the same to the operation console 3. As shown in FIG. 2, the data acquisition section 24 has a selection/addition switching circuit (MUX, ADD) 241 and an analog-digital converter (ADC) 242. The selection/addition switching circuit 241 selects the projection data detected by the detecting elements 23a of the X-ray detector 23 in response to a control signal CTL303 outputted from the central processing unit 30 or adds up them by a change in combination thereof and outputs the result of addition to the analog-digital converter 242. The analog-digital converter 242 converts the projection data selected or added up in an arbitrary combination at the selection/addition switching circuit 241 from an analog signal to a digital signal and outputs it to the central processing unit 30.

As shown in FIG. 2, the X-ray controller 25 outputs a control signal CTL251 to the X-ray tube 20 in response to a control signal CTL301 outputted from the central processing unit 30 to control the application of the X rays. The X-ray controller 25 controls, for example, a tube current, an irradiation time and the like of the X-ray tube 20. Further, the X-ray controller 25 outputs a control signal CTL252 to the X-ray tube moving section 21 in response to the control signal CTL301 outputted from the central processing unit 30 and controls the center of radiation of the X-ray tube 20 so as to move it in the body axial direction z.

As shown in FIG. 2, the collimator controller 26 outputs a control signal CTL261 to the collimator 22 in response to a control signal CTL302 outputted from the central processing unit 30 and controls the collimator 22 in such a manner that it shapes the X rays radiated from the X-ray tube 20.

As shown in FIG. 1, the rotational section 27 is cylindrical in shape and is formed with the imaging space 29 thereinside. The rotational section 27 rotates around the subject in response to a control signal CTL28 outputted from the gantry controller 28 with the body axial direction z of the subject in the imaging space 29 as the center. The rotational section 27 is equipped with the X-ray tube 20, X-ray tube moving section 21, collimator 22, X-ray detector 23, data acquisition section 24, X-ray controller 245 and collimator controller 26. The relationship of position between the subject carried in the imaging space 29 and the respective portions relatively changes in the direction of rotation of the rotational section 27. By rotating the rotational section 27, the X-ray tube 20 is capable of applying the X rays to the subject from the periphery of the subject every plural view directions. The X-ray detector 23 is able to detect the X rays transmitted through the subject every their view directions. The rotational section 27 is tilted in response to the control signal CTL28 outputted from the gantry controller 28. The rotational section 27 is inclined along the body axial direction z with the isocenter of the imaging space 29 as the center.

As shown in FIGS. 1 and 2, the gantry controller 28 outputs the control signal CTL28 to the rotational section 27, based on a control signal CTL304 outputted from the central processing unit 30 of the operation console 3 and controls the rotational section 27 so that it is rotated and tilted.

The operation console 3 will be explained.

As shown in FIG. 1, the operation console 3 includes the central processing unit 30, an input apparatus 31, a display device 32 and a memory device 33.

The central processing unit 30 is constituted of, for example, a computer and includes the tube current adjustment part 40, a controller 41 and an image generating unit 61 as shown in FIG. 1.

The tube current adjustment part 40 adjusts a tube current value supplied to the X-ray tube 20, based on a moving speed in the horizontal direction H, of the table section 101, which is controlled by a moving speed adjustment unit 102c of the subject conveyer 4, which will be described later. Here, the tube current adjustment part 40 first receives data about the speed set by the moving speed adjustment unit 102c during a scan when the table section 101 is moved in the horizontal direction H extending along the body axial direction z of the subject, and adjusts the tube current value supplied to the X-ray tube 20 such that it corresponds to the data on the speed. Described specifically, when the moving speed adjustment unit 102c sets data about a fast speed, the tube current adjustment part 40 adjusts the tube current value in such a manner that the X-ray tube 20 is driven in a high tube current value. When the moving speed adjustment unit 102c sets data about a slow speed, it adjusts the tube current value in such a manner that the X-ray tube 20 is driven in a tube current value lower than that at the fast speed.

The controller 41 is provided to control the respective portions. For example, the controller 41 accepts a scan condition inputted to the input apparatus 31 by an operator and outputs a control signal CTL30a to the respective portions, based on the scan condition to execute a scan.

Described specifically, the controller 41 outputs a control signal CTL30b to the subject conveyer 4 and allows the subject conveyer 4 to carry the subject to the imaging space 29 to move the subject. When a command for adjusting the speed of the subject moved in the imaging space 29 by the subject conveyer 4 is inputted to the input apparatus 31 by the operator, the controller 41 supplies a control signal based on the command to the moving speed adjustment unit 102c of the subject conveyer 4 to be described later and allows the moving speed adjustment unit 102c to adjust the speed at which the table section 101 supporting the subject is moved. Then, the controller 41 outputs a control signal CTL304 to the gantry controller 28 to rotate the rotational section 27 of the scanning gantry 2. Further, the controller 41 outputs a control signal CTL301 to the X-ray controller 25 such that X rays are radiated from the X-ray tube 20. Here, the controller 41 controls the X-ray controller 25 in such a manner than it supplies the tube current value adjusted by the tube current adjustment part 40 as described above to the X-ray tube 20. The controller 41 outputs a control signal CTL302 to the collimator controller 26 and thereby controls the collimator 22 to shape the X rays. The controller 41 outputs a control signal CTL303 to the data acquisition section 24 and controls the data acquisition section 24 to collect projection data obtained by the detecting elements 23a of the X-ray detector 23.

The image generating unit 61 reconstructs an image of a tomographic plane of the subject on the basis of the projection data collected by the data acquisition section 24 of the scanning gantry 2. The image generating unit 61 performs pre-treatment such as sensitivity correction, beam hardening correction, etc. on projection data based on a helical scan, for example. Thereafter, the image generating unit 61 reconstructs the so-processed data by a filtered back projection method to reconstruct and generate the image of the tomographic plane of the subject.

Here, after completion of the positioning scan, the image generating unit 61 reconstructs a first image S at a section of the subject extending along the direction in which the table section 101 is moved by the table moving section 102 on the basis of, for example, first projection data obtained by the positioning scan. For instance, the image generating unit 61 reconstructs an image about a coronal plane of the subject as a first image S.

Thereafter, the image generating unit 61 reconstructs a second image H at a section of the subject, which is associated with the first image S based on the positioning scan, on the basis of, for example, second projection data obtained by the main scan. Here, the image generating unit 61 generates an image about a coronal plane of the subject, which is similar to the first image, as the above second image, in real time with respect to the execution of the main scan.

Then, substruction processing is effected between the first image S based on the positioning scan and the second image H based on the main scan to obtain differential data. Described specifically, the first image S and the second image H are aligned so as to take the same position in the imaging region of the subject. A subtraction is done between pixel values at the same position to obtain differential data. The image generating unit 61 generates a third image P, based on the differential data obtained by the substruction processing. Even here, the image generating unit 61 generates the third image P in real time with respect to the execution of the main scan.

The input apparatus 31 of the operation console 3 is constituted of input devices such as a keyboard, a mouse, etc. The input apparatus 31 inputs various information such as a scan condition, information about the subject and the like to the central processing unit 30 on the basis of operator's input operations. For example, the input apparatus 31 has a control button through which a command for adjusting the speed of the subject moved in the imaging space 29 by the subject conveyer 4 is inputted by an operator. When the command is inputted by the operator, the input apparatus 31 supplies the command to the subject conveyer 4 through the central processing unit 30. Described specifically, the control button for adjusting the speed thereof is set such that a speed of 10 mm/s is reduced each time it is pressed once. And the input apparatus 31 supplies the command to the tube current adjustment part 40 of the central processing unit 30, where a tube current value supplied t the X-ray tube 20 is adjusted so as to correspond to data about the speed based on the command.

The display device 32 includes, for example, a CRT and displays the image about the tomographic plane of the subject reconstructed by the image generating unit 61, based on the command issued from the central processing unit 30. In the present embodiment, the display device 32 displays the image of the subject generated by the image generating unit 61 in real time with respect to the execution of the scan by the scanning gantry 2. Here, the display device 32 displays the image of the subject reconstructed by the image generating unit 61 at the section extending along the direction in which the subject is moved by the subject conveyer 4. For instance, the display device 32 displays the image about the coronal plane of the subject with the contrast agent administrated therein on its screen in real time.

The display device 32 displays the third image P generated by the image generating unit 61 based on the differential data in real time with respect to the execution of the main scan by the scanning gantry 2.

The memory device 33 is made up of a memory and stores therein various data such as the images of the subject reconstructed by the image generating unit 61, and programs and the like. In the memory device 33, the data stored therein are accessed by the central processing unit 30 as needed.

The subject conveyer 4 will be explained.

The subject conveyer 4 is provided to convey the subject between the inside and outside of the imaging space 29.

Figure 4:
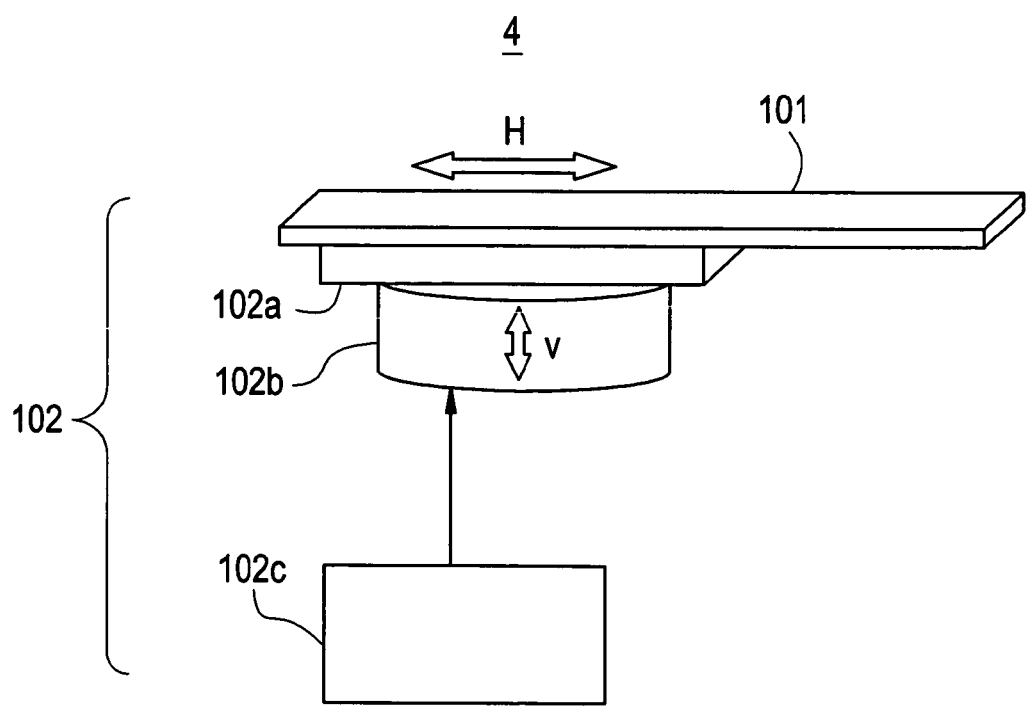
FIG. 4 is a configuration diagram illustrating a construction of a subject conveying section in the X-ray CT apparatus illustrative of the embodiment according to the present invention.

FIG. 4 is a configurational diagram showing the construction of the subject conveyer 4.

As shown in FIG. 4, the subject conveyer 4 has the table section 101 and the table moving section 102.

The table section 101 includes a table formed with a mounting surface on which the subject is placed, and supports the subject on the mounting surface. As shown in FIG. 4, the table section 101 is moved by the table moving section 102 in a horizontal direction H extending along the body axial direction z of the subject placed on the mounting surface and a vertical direction V orthogonal to a horizontal plane, and carried into the imaging space 29. Then, the table section 101 is moved within the imaging space 29 according to the scan condition to shift the position of the imaging region in which the subject is scanned.

The table moving section 102 is provided to move the table section 101. The table moving section 102 moves the table section 101 in such a manner that its position changes between the inner and outer sides of the imaging space 29. Then, the table moving section 102 moves the table section 101 within the imaging space 29 according to the scan condition to thereby shift the position of an imaging region in which the subject is scanned. As shown in FIG. 4, the table moving section 102 has a horizontal moving unit 102a, a vertical moving unit 102b and a moving speed adjustment unit 102c.

The horizontal moving unit 102a moves the table section 101 in the horizontal direction H. The horizontal moving unit 102a is provided with, for example, a roller type moving mechanism (not shown). A roller is driven by an actuator (not shown) to move the table section 101 in the horizontal direction H.

The vertical moving unit 102b moves the table section 101 in the vertical direction V. The vertical moving unit 102b is equipped with an arm type moving mechanism (not shown). The angle formed between two crossed arms is changed by an actuator (not shown) to thereby move the table section 101 in the vertical direction V.

When the scanning gantry 2 scans the subject, the moving speed adjustment unit 102c adjusts the speed at the time that the table 101 is moved in the horizontal direction H by the horizontal moving unit 102a of the table moving section 102. When a command for adjusting the moving speed of the table section in the horizontal direction H is inputted to the input apparatus 31 by the operator, the moving speed adjustment unit 102c allows the horizontal moving unit 102a of the table moving section 102 to adjust the speed of the table section 101 moved in the horizontal direction H on the basis of the command. Described specifically, when a subject with a contrast agent administrated therein is helically scanned and an image displayed by the display device 32 in real time is observed by the operator, the operator inputs a command for lowering the moving speed of the table section 101 so as to match with the progress of the displayed image of contrast agent to the input apparatus 31. The moving speed adjustment unit 102c accepts the command via the central processing unit 30 to allow the horizontal moving unit 102a to control the moving operation of the table section 101. The speed at which the table section 101 is moved in the horizontal direction H is reduced by 10 mm/s, for example.

Incidentally, the X-ray CT apparatus 1 according to the present embodiment is equivalent to a radiation imaging apparatus of the present invention. The scanning gantry 2 employed in the present embodiment is equivalent to a scan section of the present invention. The X-ray tube 20 employed in the present embodiment is equivalent to a radiation tube of the present invention. The display device 32 employed in the present embodiment is equivalent to a displayer of the present invention. The tube current adjustment part 40 employed in the present embodiment corresponds to a tube current adjuster of the present invention. The image generating unit 61 employed in the present embodiment is equivalent to an image generator of the present invention. The table section 101 employed in the present embodiment is equivalent to a table unit of the present invention. The table moving section 102 employed in the present embodiment is equivalent to a table mover of the present invention. The moving speed adjustment unit 102c employed in the present embodiment corresponds to a speed adjuster of the present invention. The positioning scan executed in the present embodiment corresponds to a first scan of the present invention. The main scan executed in the present embodiment is equivalent to a second scan of the present invention.

The operation of photographing or imaging a subject using the X-ray CT apparatus 1 of the present embodiment will be explained.

Figure 5:
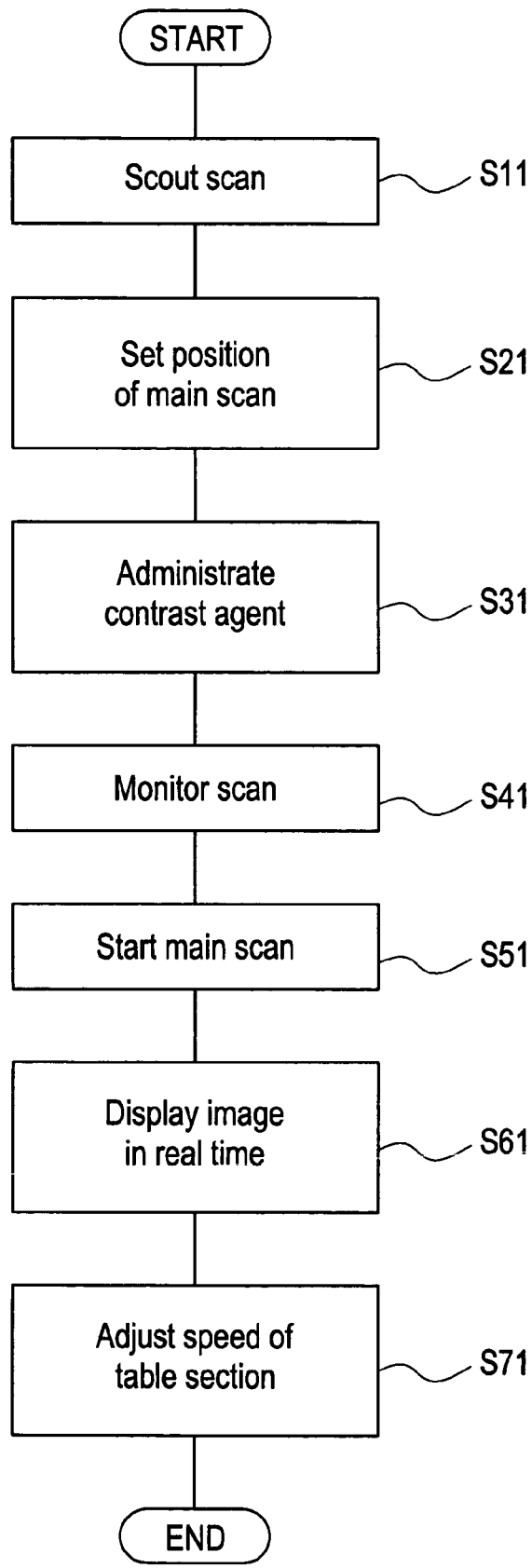
FIG. 5 is a flow chart showing the operation of the X-ray CT apparatus illustrative of the embodiment according to the present invention.

FIG. 5 is a flowchart showing the operation of the X-ray CT apparatus 1 of the present embodiment.

As shown in FIG. 5, a positioning scan is first executed (S11).

Here, in order to decide the position of the subject to be scanned upon the main scan, the X-ray tube 20 applies X rays to the subject from the direction extending along the vertical direction, for example. The image generating unit 61 generates an image about a coronal plane of the subject as a positioning image on the basis of projection data of the subject.

For instance, the scanning gantry 2 executes a positioning scan in accordance with a helical scan system to obtain first projection data. A first image S about a coronal plane of the subject is generated based on the first projection data obtained by the positioning scan. Described specifically, the image generating unit 61 reconstructs the projection data of the subject obtained by the positioning scan with respect to the coronal plane of the subject and generates the first image S as a positioning image.

FIG. 6 is a diagram showing first images S corresponding to positioning images. The first images arranged in time series in the order of FIGS. 6(A), 6(B) and 6(C) are shown in FIG. 6.

As shown in each of FIGS. 6(A), 6(B) and 6(C), the image generating unit 61 updates an image about a coronal plane of the subject for each scan rotated once about the subject and generates a first image S as a positioning image.

Next, the position of the main scan is set (S21).

Here, for instance, an operator inputs position information about the subject scanned by means of the main scan to the input apparatus 31 on the basis of the first images S corresponding to the positioning images generated in the above-described manner.

Next, a contrast agent is administrated in the subject (S31).

Here, the operator mixes a contrast agent into fluid flowing into the subject so as to correspond to the position of the subject scanned by the main scan. Described specifically, a contrast agent is administrated in the blood vessels of the subject and mixed into the blood flowing into the subject.

Next, a monitor scan is executed (S41).

Here, the scanning gantry 2 scans an imaging region for the subject with the contrast agent administrated therein. The display device 32 displays an image of the subject in real time. And the operator monitors the state of traveling of the contrast agent through the image displayed by the display device 32.

FIG. 7 is a diagram showing the manner of the monitor scan. In FIG. 7, FIG. 7(A) shows the region of the subject subjected to the monitor scan in a first image S corresponding to a positioning image, and FIG. 7(B) shows a monitor image M displayed upon the monitor scan.

Upon the monitor scan as shown in FIG. 7(A), the region RM of the subject, corresponding to the first image S indicative of the positioning image is monitor-scanned. As shown in FIG. 7(B), the monitor image M is displayed corresponding to the first image S corresponding to the positioning image. Here, the image obtained by the positioning scan and the image obtained by the monitor scan are subjected to substruction processing. A differential image constituted of a differential value therebetween is generated and displayed as a monitor image M. Described specifically, an image indicative of arteries in the subject, which are stained with the contrast agent, is displayed as a monitor image M.

Next, the main san is started (S51).

Here, the operator monitors the state of progress of the contrast agent and confirms that an image about the contrast agent has been displayed. Thereafter, the operator inputs a command for starting the main scan to the input apparatus 31. Then, the scanning gantry 2 executes the main scan in accordance with the scan start command inputted from the operator. In a manner similar to the positioning scan, for example, the scanning gantry 2 performs the main scan by the helical scan system to obtain second projection data of the subject.

Next, the image obtained by the main scan is displayed in real time (S61).

Here, the image generating unit 61 reconstructs the projection data in real time with respect to the execution of the main scan by the scanning gantry 2 to thereby generate an image of the subject. On the basis of the second projection data obtained by the main scan, for example, the image generating unit 61 generates a second image H about a coronal plane in real time as a section extending along the direction in which the subject is moved by the subject conveyer 4. Described specifically, the image generating unit 61 generates, as a second image H, an image about a coronal plane of the subject, which is similar to the first image S, in real time with respect to the execution of the main scan by the scanning gantry 2. As the second image H, such an image so as to contain the contrast agent traveling within the subject is obtained from the first image S, for example.

A third image P is generated based on differential data based on substruction processing between the first image S and the second image H.

Figure 8A:
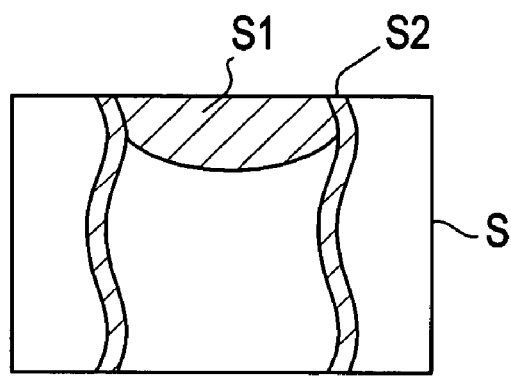
FIG. 8A is a diagram showing an embodiment of a positioning image generated by using the X-ray CT apparatus.
Figure 8B:
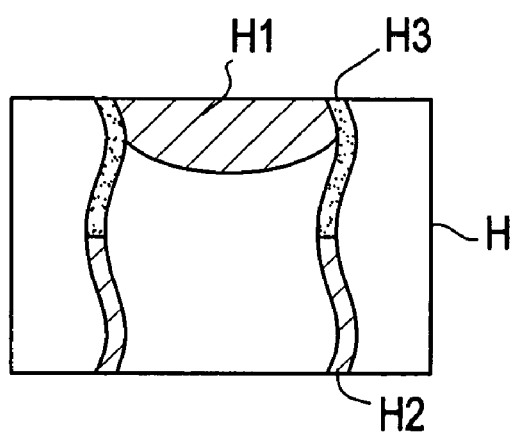
FIG. 8B is a diagram showing an embodiment of an image generated after administering a contrast agent within the subject.
Figure 8C:
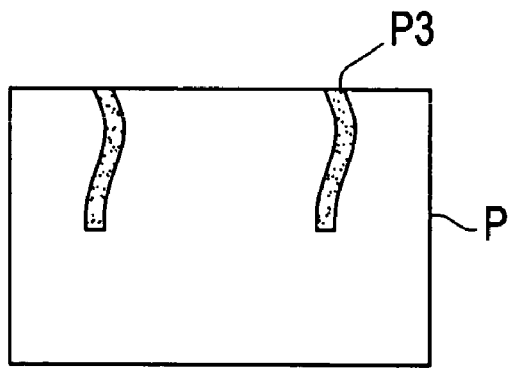
FIG. 8C is a diagram showing an embodiment of an image generated from subtraction processing between the images of FIGS. 8A and 8B.

FIG. 8 is a diagram showing the manner in which the image generating unit 61 generates a third image P using a first image S and a second image H. In FIG. 8, FIG. 8(A) shows the first image S, FIG. 8(B) shows the second image H and FIG. 8(C) shows the third image P, respectively.

As shown in FIG. 8, here, the image generating unit 61 first extracts the corresponding portion of the first image S of the same position as an imaging region of the subject, corresponding to the second image H generated in real time. Then, the image generating unit 61 aligns the first image S and the second image H such that they are placed in the same position in the imaging region of the subject, and performs subtraction between pixel values at the same position to obtain differential data. The second image H includes a plurality of contrast agent portions H3. The image generating unit 61 generates the corresponding third image P, based on the differential data in real time with respect to the execution of the main scan. As shown in FIG. 8(C), the third image P is one in which portions corresponding to a tissue portion S1 and each blood vessel portion S2 are eliminated from the first image S and portions corresponding to a tissue portion H1 and each blood vessel portion H2 are eliminated from the second image H. Thus, images corresponding to contrast agent portions P3 that travel in the subject are obtained.

The third image P is displayed in real time.

Here, the display device 32 displays the third image P generated by the image generating unit 61 using the differential data, in real time with respect to the execution of the main scan by the scanning gantry 2. The display device 32 displays the first image S and the third image P in parallel in such a manner that the third image P is aligned with the first image S corresponding to the positioning image at the position of the subject associated with the third image P generated in real time, for example.

When the operator refers to the subject's images displayed in real time and inputs a command for adjusting the speed of the table section 101, the speed of the table section 101 is adjusted (S71).

When the scanning gantry 2 performs the main scan on the subject according to the main scan condition, the moving speed adjustment unit 102c adjusts the speed at which the table section 101 is moved in the horizontal direction H by the horizontal moving unit 102a. Described specifically, the operator inputs a command for adjusting the speed of the table section 101 to the input apparatus by referring to the third image P displayed in real time. Then, the moving speed adjustment unit 102c adjusts the speed of the table section 101 moved in the horizontal direction H by the horizontal moving unit 102a on the basis of the command for adjusting the speed thereof moved in the horizontal direction H.

Figure 9A:
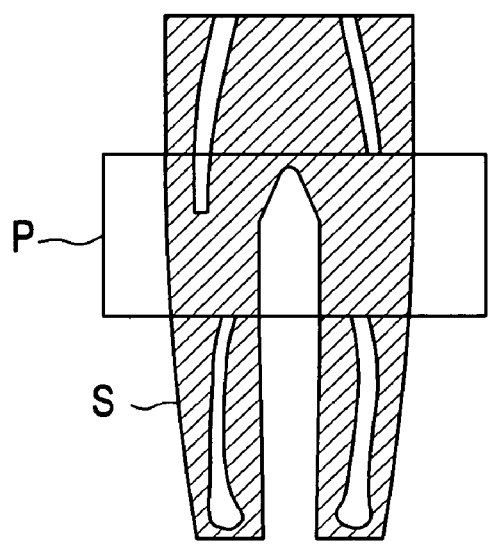
FIG. 9A is a diagram illustrating an embodiment of a method for adjusting a speed of a table section during a main scan.
Figure 9B:
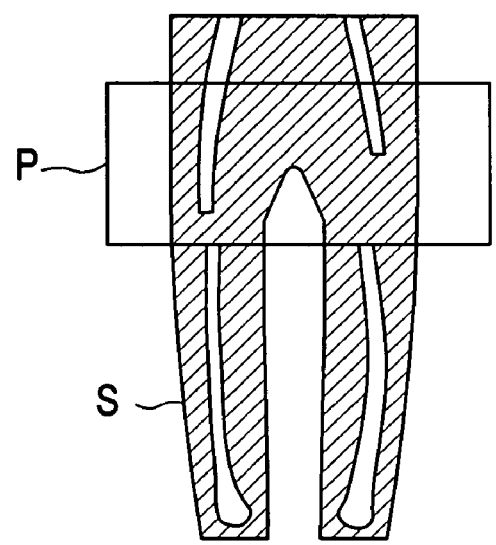
FIG. 9B is a diagram illustrating another embodiment of a method for adjusting a speed of a table section during a main scan.

FIG. 9 is a diagram showing the manner in which the speed of the table section 101 is adjusted during the main scan. In FIG. 9, FIG. 9(A) shows a third image P at the time that the operator gives an instruction for deceleration, and FIG. 9(B) shows a third image P at the time that the operator gives an instruction for acceleration.

When the speed at which subject's blood vessels are stained is slower than the speed of the table section 101 as shown in FIG. 9(A), the operator inputs a command for lowering the moving speed of the table section 101 to the input apparatus 31. The moving speed adjustment unit 102c causes the horizontal moving unit 102a to control the moving operation of the table section 101 in response to the command. The moving speed adjustment unit 102c reduces the moving speed of the table section 101 by 10 mm/s, for example and matches the moving speed of the table section 101 with the progress or traveling of the image of the contrast agent displayed by the display device 32 in real time.

When the speed at which the subject's blood vessels are stained is faster than the speed of the table section 101 as shown in FIG. 9(B), the operator inputs a command for increasing the moving speed of the table section 101 to the input apparatus 31. The moving speed adjustment unit 102c controls the horizontal moving unit 102a to increase the moving speed of the table section 101 by 10 mm/s, for example in response to the command and matches the moving speed of the table section 101 with the progress of the image of the contrast agent displayed by the display device 32 in real time.

At this time, the tube current adjustment part 40 adjusts a tube current value supplied to the X-ray tube 20 on the basis of the moving speed in the horizontal direction H, of the table section 101, which speed is adjusted by the moving speed adjustment unit 102c. Here, the tube current adjustment part 40 accepts, during the scan, data about the speed set by the moving speed adjustment unit 102c when the table section 101 is moved in the horizontal direction H extending along the body axial direction z of the subject. Then, the tube current adjustment part 40 adjusts the tube current value supplied to the X-ray tube 20 so as to correspond to the data about the speed. Described specifically, when the moving speed adjustment unit 102c sets data about a fast speed, the tube current adjustment part 40 adjusts the tube current value in such a manner that the X-ray tube 20 is driven in a high tube current value. When the moving speed adjustment unit 102c sets data about a slow speed, the tube current adjustment part 40 adjusts the tube current value in such a manner that the X-ray tube 20 is driven in a tube current value lower than that at the fast speed.

When a scan position has reached a completion position, the scan is finished.

In the present embodiment as described above, the moving speed adjustment unit 102c adjusts the speed at which the table section 101 is moved in the imaging space 29 when the scanning gantry 2 scans the subject, based on the command issued from the operator. Therefore, even when the contrast agent is administrated in the subject and imaging is done, the scan can be done in accordance with the speed of the contrast agent that travels in the blood vessels of the subject.

In the present embodiment as well, the tube current adjustment part 40 adjusts the tube current value supplied to the X-ray tube 20 on the basis of the speed at the scan of the table section 101, which is adjusted by the moving speed adjustment unit 102c. Therefore, the X rays can be utilized efficiently and the amount of exposure to radiation can be reduced to enhance safety.

Further, in the present embodiment, the image generating unit 61 reconstructs and generates the image about the coronal plane corresponding to the section of the subject extending along the direction in which the table section 101 is moved by the table moving section 102. The display device 32 displays the sectional image reconstructed by the image generating unit 61. Therefore, it becomes easy to confirm whether imaging is done corresponding to the state of traveling of the contrast agent, for example, thus making it possible to reduce the operation of the operator.

Furthermore, in the present embodiment, the scanning gantry 2 executes the first scan for applying the X rays to the imaging region of the subject to generate the first projection data. Thereafter, the scanning gantry 2 performs the second scan for applying the X rays to the image region of the subject with the contrast agent administrated therein to generate the second projection data. Then, the image generating unit 61 reconstructs the first image about the section of the subject extending in the direction in which the table section 101 is moved by the table moving section 102, on the basis of the first projection data. Thereafter, the image generating unit 61 reconstructs the second image about the section of the subject, corresponding to the first image on the basis of the second projection data in such a manner that real time is taken with respect to the execution of the second scan. Along with it, the image generating unit 61 generates the third image, based on the data about the differential data by the substruction processing between the first and second images. The display device 32 displays the third image generated by the image generating unit 61 in real time with respect to the execution of the second scan. Therefore, the present embodiment is capable of easily confirming whether the imaging is done corresponding to the state of traveling of the contrast agent, and reducing the operation of the operator.

Thus, the present embodiment is capable of enhancing operability and executing imaging efficiently.

Incidentally, upon the implementation of the present invention, the present invention is not limited to the above embodiment. Various modifications can be adopted.

Although the above embodiment explains, for instance, the example using the X rays as radiation, the present invention is not limited to it. For example, radiation such as gamma rays may be used.

Many widely different embodiments of the invention may be constructed without departing from the spirit and the scope of the present invention. It should be understood that the present invention is not limited to the specific embodiments described in the specification, except as defined in the appended claims.

The invention claimed is:

1. An X-ray computed tomography (CT) apparatus comprising:
    a table unit configured to support a subject to be examined;
    a table moving unit configured to move the table unit;
    a scan section configured to apply radiation to the subject supported by the table unit in an imaging space, wherein said scan section is configured to execute a first scan to apply the radiation to an imaging region of the subject, wherein said scan section is configured to apply the radiation to the imaging region of the subject to generate first projection data, wherein said scan section is configured to thereafter execute a second scan to apply the radiation to the imaging region of the subject with a contrast agent administrated therein to generate second projection data;
    an image generator configured to reconstruct a first tomographic image of a section of the subject along a direction in which the table unit is moved on the basis of the first projection data, wherein said image generator is configured to thereafter reconstruct a second tomographic image of the subject corresponding to the first tomographic image on the basis of the second projection data in real time with respect to the execution of the second scan, and wherein said image generator is configured to generate a third image on the basis of differential data based on subtraction processing between the first tomographic image and the second tomographic image;
    a display device configured to display the third image generated by the image generator in real time with respect to the execution of the second scan; and
    an input unit configured to receive a scan condition, wherein said input unit is configured to receive a change in a speed of the table unit in real time during the second scan of the subject including the contrast agent, wherein the change in the speed of the table unit is based on a speed of the contrast agent visible within the real time display of the third image.

2. The X-ray CT apparatus according to claim 1, wherein the scan section executes the first scan and the second scan so as to helically scan the periphery of the subject along the direction in which the table unit is moved.

3. The X-ray CT apparatus according to claim 2, wherein the table moving unit has a speed adjustment unit which adjusts the moving speed of the table unit when the scan section scans the subject.

4. The X-ray CT apparatus according to claim 2, wherein the scan section includes a radiation tube which applies the radiation to the subject in accordance with a tube current value, and a tube current adjuster which adjusts the tube current value on the basis of the speed of the table unit.

5. The X-ray CT apparatus according to claim 2, wherein X rays are radiated as the radiation.

6. The X-ray CT apparatus according to claim 1, wherein the table moving unit has a speed adjustment unit which adjusts the moving speed of the table unit when the scan section scans the subject.

7. The X-ray CT apparatus according to claim 6, wherein the scan section includes a radiation tube which applies the radiation to the subject in accordance with a tube current value, and a tube current adjuster which adjusts the tube current value on the basis of the speed of the table unit.

8. The X-ray CT apparatus according to claim 6, wherein X rays are radiated as the radiation.

9. The X-ray CT apparatus according to claim 1, wherein the scan section includes a radiation tube which applies the radiation to the subject in accordance with a tube current value, and a tube current adjuster which adjusts the tube current value on the basis of the speed of the table unit.

10. The X-ray CT apparatus according to claim 9, wherein X rays are radiated as the radiation.

11. The X-ray CT apparatus according to claim 1, wherein X rays are radiated as the radiation.

* * * * *